(12) United States Patent
Birkbeck

(10) Patent No.: US 8,445,727 B2
(45) Date of Patent: May 21, 2013

(54) BICYCLO-KETONES AS PERFUMING INGREDIENTS

(75) Inventor: Anthony A. Birkbeck, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 13/641,931

(22) PCT Filed: May 12, 2011

(86) PCT No.: PCT/IB2011/052084
§ 371 (c)(1),
(2), (4) Date: Oct. 18, 2012

(87) PCT Pub. No.: WO2011/154859
PCT Pub. Date: Dec. 15, 2011

(65) Prior Publication Data
US 2013/0045906 A1    Feb. 21, 2013

(30) Foreign Application Priority Data
Jun. 8, 2010    (EP) .................................. 10165239

(51) Int. Cl.
*C07C 49/115* (2006.01)
(52) U.S. Cl.
USPC .......................................... 568/374; 512/18
(58) Field of Classification Search ...... 568/374; 512/18
See application file for complete search history.

(56) References Cited

U.S. PATENT DOCUMENTS

| 6,184,419 B1 | 2/2001 | Berg-Schultz et al. ........ 568/374 |
| 2011/0014143 A1 | 1/2011 | Chapuis et al. ................. 424/65 |

FOREIGN PATENT DOCUMENTS

| GB | 1 336 101 A | 11/1973 |
| GB | 1336101 | * 11/1973 |
| WO | WO 2009/128026 | * 10/2009 |
| WO | WO 2009/128026 A1 | 10/2009 |

OTHER PUBLICATIONS

International Search Report and Written Opinion of the International Searching Authority, application No. PCT/IB2011/052084, mailed Aug. 26, 2011.
Olah et al., "New One-Pot Preparation of α, β-Unsaturated Carboxylic Acid Esters from Carbonyl Compounds," Synthesis, 7:537-538 (1988).
Reusch et al., "A Stereospecific Photochemical Addition of Acetone to Norbornylene," Journal of Organic Chemistry, 27(5):1882-1883 (1962).

* cited by examiner

Primary Examiner — John Hardee
(74) Attorney, Agent, or Firm — Winston & Strawn LLP

(57) ABSTRACT

A compound and a method to confer, enhance, improve or modify the odor properties of a perfuming composition or of a perfumed article, to confer a green allylic, glycolate and fruity-pineapple odor, by adding the compound thereto. The compound has formula (I):

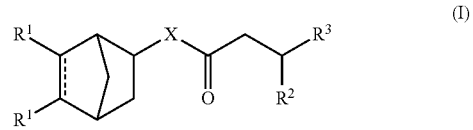

wherein the dotted line represents a carbon-carbon single bond or a carbon-carbon double bond; one $R^1$ represents a hydrogen atom and the other represents a hydrogen atom or a methyl or ethyl group; X representing a $C=CH_2$ or $C=CHCH_3$ group or a $CHR^2$ group, each $R^2$ representing a hydrogen atom or a methyl or ethyl group; and $R^3$ represents a
a group of formula $CR^4=C(R^4)_2$, or
a group of formula

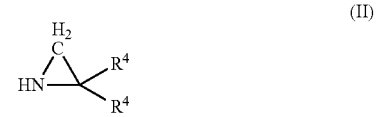

each $R^4$ representing a hydrogen atom or a methyl or ethyl group. The compound is in the form of a pure enantiomer or a mixture thereof.

20 Claims, No Drawings

BICYCLO-KETONES AS PERFUMING INGREDIENTS

TECHNICAL FIELD

The present invention relates to the field of perfumery. More particularly, it concerns the use as perfuming ingredient of some bicyclo-ketone derivatives of formula (I), as shown herein below. In addition, the present invention comprises also aspects such as the ones wherein the invention's compound is part of a perfuming composition or of a perfuming consumer product.

PRIOR ART

To the best of our knowledge, the present compounds are new chemicals.

The compounds with the closest chemical structure and being described as having valuable organolepic properties are those reported in U.S. Pat. No. 6,184,419, and in particular 2-cyclohexyl-1,6-heptadien-3-one. However these prior art compounds are reported as having a green-galbanum (i.e. a acidic/aggressive and bitter green note) and fruity odor notes, plus other notes which are absent for the odor of the present invention's compounds, in other words a quite different note.

The compounds with the closest chemical structure and being described as having valuable organolepic properties are those reported in WO 09/128026, and in particular 1-cyclohexyl-5-hexen-2-one. However these prior art compounds are reported as having a fruity-pineapple odor note, in other words a quite different odor and tonality.

Nothing in the two prior arts suggests that the invention's compounds could have their specific odor (as reported further below) or even an odor at all.

DESCRIPTION OF THE INVENTION

We have now surprisingly discovered that a $C_{13}$-$C_{16}$ compound of formula

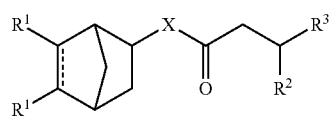

(I)

wherein the dotted line represents a carbon-carbon single bond or a carbon-carbon single or double bond;
one $R^1$ is a hydrogen atom and the other $R^1$ represents a hydrogen atom or a methyl or ethyl group;
X represents a C=$CH_2$ or C=$CHCH_3$ group or a $CHR^2$ or $CHR^2CHR^2$ group;
each $R^2$, independently from each other, represents a hydrogen atom or a methyl or ethyl group; and
$R^3$ represents a
  a group of formula $CR^4$=$C(R^4)_2$, each $R^4$ representing, independently from each other, a hydrogen atom or a methyl or ethyl group; or a group of formula

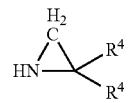

(II)

$R^4$ having the same meaning as above; and
said compound being in the form of a pure enantiomer or a mixture thereof;
can be used as perfuming ingredient, for instance to impart an odor characterized by a duality of green allylic, glycolate type note and natural fruity-pineapple notes.

According to a particular embodiment of the invention, said compounds (I) are those wherein the dotted line represents a carbon-carbon single bond;
one $R^1$ is a hydrogen atom and the other $R^1$ represents a hydrogen atom or a methyl or ethyl group;
X represents a C=$CH_2$ group or a $CHR^2$ or $CHR^2CHR^2$ group,
each $R^2$, independently from each other, represents a hydrogen atom or a methyl or ethyl group,
$R^3$ represents a
  a group of formula $CR^4$=$C(R^4)_2$, $R^4$ representing, simultaneously or independently from each other, a hydrogen atom or a methyl group.

According to a particular embodiment of the invention, said compound (I) is of formula

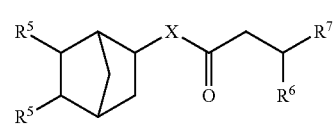

(II)

wherein one $R^5$ is a hydrogen atom and the other $R^5$ represents a hydrogen atom or a methyl group;
X represents a group as defined in formula (I);
$R^6$ represents a hydrogen atom or a methyl group; and
$R^7$ represents a group of formula $CR^8$=$CHR^8$, each $R^8$, independently from each other, represents a hydrogen atom or a methyl group.

According to any one of the above embodiments of the invention, X may represent a C=$CH_2$ or a $CHR^6$ or a $CHR^6CHR^6$ group, wherein each $R^6$ is as defined above. In particular X may represent a $CHR^6$ or a $CHR^6CHR^6$ group, such as a $CH_2$ or a $CH_2CH_2$ group, or simply represent a $CHR^6$ or $CH_2$ group.

According to any one of the above embodiments of the invention, each $R^1$/$R^5$ is a hydrogen atom.

According to any one of the above embodiments of the invention, each $R^2$/$R^6$ is a hydrogen atom.

According to any one of the above embodiments of the invention, $R^3$/$R^7$ is a group of formula CH=$CH_2$.

According to any one of the above embodiments of the invention, each $R^8$/$R^4$ is a hydrogen atom.

The compound (I), as defined above in any one of the embodiments, is also an object of the present invention since it is a novel compound.

According to any one of the above embodiments of the invention, said compounds (I) are $C_{13}$-$C_{14}$ compounds.

For the sake of clarity, by the expression "wherein the dotted line represents a carbon-carbon single bond or a carbon-carbon double bond", or the similar, it is meant the normal meaning understood by a person skilled in the art, i.e. that the whole bonding (solid and dotted line) between the carbon atoms connected by said dotted line, e.g. carbon 2 and 3, is a carbon-carbon single or double bond.

As mentioned above, the compound (I) can be in the form of a pure enantiomer or a mixture thereof. According to any one of the above embodiments, the invention concern a mixture of endo and exo diastereomers of formulae

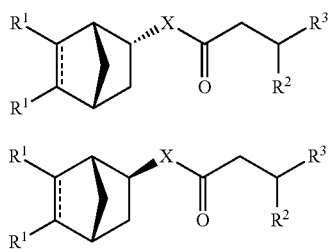

or for compound (II) a mixture of diastereomers of formulae

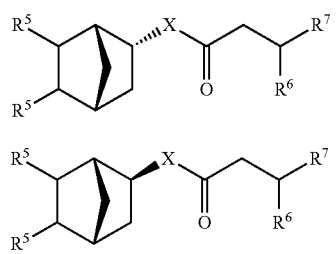

wherein all the $R^1$ to $R^7$, X and dotted lines have the same meaning as indicated above.

According to particular embodiment of the invention, said mixture of compounds (I') and (I"), or (II') and (II"), comprises at least 50%, or even at least 60%, of diastereomer (I'), or (II'), the percentage being relative to the total weight of the mixture.

As specific examples of the invention's compounds one may cite, as non-limiting example, 1-(bicyclo[2.2.1]heptan-2-yl)-hex-5-en-2-one (in particular in the form of a 70/30 mixture of 1-((1RS,2RS,4SR)-bicyclo[2.2.1]heptan-2-yl)-hex-5-en-2-one and 1-((1RS,2SR,4SR)-bicyclo[2.2.1]heptan-2-yl)-hex-5-en-2-one) which possesses an odor which associates a green note of the glycolate type (i.e. relatively sweet and not aggressive) with a fruity-pineapple note of similar intensity, and in addition said compound possesses also a marine note. The overall note is very strong, especially for such a type of odor. The olfactive profile reminds of a well balanced synthesis of the green notes of glycolates (e.g. allyl amyl glycolate or allyl phenoxyacetate) and the pineapple note of some allylic derivatives (e.g. allyl heptanoate or caproate).

As other example, one may cite one compound very appreciated by the perfumer, namely 1-((1RS,4SR)-bicyclo[2.2.1]heptan-2-yl)hept-6-en-3-one which possesses an odor characterized by a duality of green allylic, glycolate type notes and natural fruity-pineapple notes, but which differentiate from the above example by having also a very slight additional hint of green note, and by being less powerful than the one cited above.

As other specific, but non-limiting, examples of the invention's compounds, one may cite the following ones in Table 1:

TABLE 1

Invention's compounds and their odor properties

| Compound structure and name | Odor notes |
|---|---|
| 2-(bicyclo[2.2.1]heptan-2-yl)hepta-1,6-dien-3-one | Odor possessing amyl glycolate and pineapple notes. |
| 1-((1RS,2SR,4SR)-bicyclo[2.2.1]heptan-2-yl)hex-5-en-2-one | A strong odor associating a green note of the glycolate type with a fruity-pineapple note of similar intensity. Close to the odor of 1-(bicyclo[2.2.1]heptan-2-yl)-hex-5-en-2-one. |
| 1-((1RS,4RS)-bicyclo[2.2.1]hept-5-en-2-yl)hex-5-en-2-one | Close to the odor of 1-(bicyclo[2.2.1]heptan-2-yl)-hex-5-en-2-one, but differentiates by having a fatty note and being weaker than the above-mentioned compound. |

According to a particular embodiment of the invention, the compounds of formula (I) are 1-(bicyclo[2.2.1]heptan-2-yl)-hex-5-en-2-one, and in particular a mixture of 1-((1RS,2RS,4SR)-bicyclo[2.2.1]heptan-2-yl)-hex-5-en-2-one and 1-((1RS,2SR,4SR)-bicyclo[2.2.1]heptan-2-yl)-hex-5-en-2-one), 1-((1RS,4SR)-bicyclo[2.2.1]heptan-2-yl)hept-6-en-3-one or 1-((1RS,2SR,4SR)-bicyclo[2.2.1]heptan-2-yl)hex-5-en-2-one.

When the odor of the invention's compound (I) is compared with that of the prior art compounds disclosed in U.S. Pat. No. 6,184,419, then the invention's compounds distinguish themselves by having the tonality of the green note which is not bitter, sweeter and much less aggressive than the prior art compounds (a galbanum note being associated with the an acidic, aggressive, chemical and bitter green, pyrazinic note). Furthermore, while the invention's compounds possess green and fruity notes of similar intensity, the compounds disclosed in U.S. Pat. No. 6,184,419 possess a galbanum character much stronger than the pineapple one. Another important difference is that present compounds (I) are lacking, or not possessing significant, metallic, woody, cassis or anisic notes, to the contrary of the compounds disclosed in U.S. Pat. No. 6,184,419.

When the odor of the invention's compound (I) is compared with that of the prior art compounds disclosed in WO 09/128026, then the invention's compounds distinguish themselves by having a green note.

Said differences lend the invention's compounds and the prior art compounds to be each suitable for different uses, i.e. to impart different organoleptic impressions.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- and Gehermittel in Lebensmittel, Band 2 der Schriftenreihe Lebensmittelchemie, Lebensmittelqualität, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery.

Furthermore, the invention's compound can also be advantageously used in all the fields of modern perfumery, i.e. fine or functional perfumery, to positively impart or modify the odor of a consumer product into which said compound (I) is added. Consequently, a perfuming consumer product which comprises:

i) as perfuming ingredient, at least one compound of formula (I), as defined above; and
ii) a fine or functional perfumery base;
is also an object of the present invention.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "fine or functional perfumery base" we mean here a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the fine or functional perfumery base do not warrant a more detailed description here, which in any case would not be exhaustive, the skilled person being able to select them on the basis of his general knowledge and according to the nature and the desired effect of said product.

Non-limiting examples of suitable fine or functional perfumery base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oils or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 10% by weight, or even more, of the compounds of the invention based on the weight of the composition into which they are incorporated. Concentrations lower than these, such as in the order of 0.001% to 5% by weight, can be used when these compounds are incorporated into perfumed articles, percentage being relative to the weight of the article.

The invention's compounds can be prepared according to a method a described in the examples.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of Compounds of Formula (I)

Preparation of 1-(bicyclo[2.2.1]heptan-2-yl)-hex-5-en-2-one a) Methyl 2-((1RS,4SR)-bicyclo[2.2.1]heptan-2-yl)acetate In a s/s autoclave, palladized charcoal (2.0 g, 10% Pd/C) was added to the methyl 2-((1RS,4SR)-bicyclo[2.2.1]hept-5-en-2-yl)acetate [ref, G. A. Olah, A-H. Wu, O. Farooq, G. K. Surya Prakash, *Synthesis*, 1988, 537-538.] (65.5 g, 0.39 mol) and the suspension evacuated, then purged with hydrogen gas (3×). The suspension was then stirred under an atmosphere of hydrogen gas (85 bars) for 12 hours. The suspension was filtered through a short plug of celite, washed with ethyl acetate and the filtrate concentrated in vacuo. The residue was further purified by bulb to bulb distillation 150-160° C. at 0.3 mbar and gave the saturated ester, 63.1 g, 95% as a colorless oil. (mixture of endo/exo isomers, 70:30).

$^1H$ NMR: 3.65 (s, 3H), 2.33 (d, J=1, 0.6H), 2.31 (s, 1.4H), 2.31-2.10 (m, 3H), 1.97 (bs, 0.3H), 1.93-1.78 (m, 1.4H), 1.56-1.42 (m, 3H), 1.39-1.01 (m, 2H), 0.66 (ddd, J=12.2, 5.3, 2.4, 0.7H).

$^{13}C$ NMR: 174.1, 173.7 (s), 51.4, 51.38 (q), 41.2 (d), 41.1 (t), 40.2 (d), 39.8 (t), 38.4 (t), 37.4 (t), 37.1 (d), 36.8 (d), 36.6 (d), 36.4, 35.2, 30.0, 29.8, 28.6, 22.6 (t).

b) 2-((1RS,4SR)-bicyclo[2.2.1]heptan-2-yl)ethanol

A solution of the saturated ester obtained under a) (63.1 g, 0.375 mol) in anhydrous diethyl ether (200 mL) was added slowly dropwise to a mechanically stirred suspension of $LiAlH_4$ (10 g 0.26 mol) in anhydrous diethyl ether (300 mL) at ambient temperature. Exothermic reaction allowed to warm to a gentle reflux. The suspension was allowed to cool and stirred for a further 12 hours. The suspension was cooled to 0-5° C. and water (10 ml) was added cautiously, followed by 15% aqueous NaOH (10 ml) and then water (30 ml). Anhydrous $MgSO_4$ was then added, the suspension stirred for a further 30 minutes then filtered. The filter cake was washed with ether, then the combined filtrate concentrated in vacuo to yield the alcohol, 51.6 g, 98%.

1H NMR: 3.62 (t, J=7.2, 2H), 2.19, (bs, 0.3H), 2.15 (t, J=4.6, 0.7H), 2.09 (t, J=3.8), 1.96 (bs, 0.3H), 1.90-1.80 (m, 0.7H), 1.76 (dddd, J=11.8, 11.3, 4.5, 2.7, 1H), 1.66-1.25 (m, 7H), 1.19-1.00 (m, 2H), 0.63 (ddd, J=11.6, 5.0, 2.5, 0.7H).

$^{13}$C NMR: 62.6, 61.6 (t), 41.2, 40.0 (d), 39.9 (t), 38.4 (d), 38.1 (t), 37.0 (d), 36.9 (t), 36.6, 36.3 (d), 36.0, 35.3, 30.4, 30.1, 28.8, 22.5 (t).

c) 2-((1RS,4SR)-bicyclo[2.2.1]heptan-2-yl)acetaldehyde

Pyridinium chlorochromate (116 g, 0.54 mol) was suspended in dichloromethane (1000 ml) containing silica gel (150 g). After 15 minutes of mechanical stirring, a solution of the alcohol obtained under b) (54 g, 0.385 mol) in dichloromethane (400 ml) was added rapidly dropwise. After 30 minutes a further portion of pyridinium chlorochromate (5 g) was added and the suspension stirred for a further 30 minutes, then diluted with ether (500 ml). Added celite (25 g) and stirred for a further 15 minutes, then filtered through a plug of celite/silica. The filter cake was washed with ether and the combined filtrate was concentrated in vacuo to yield the pure aldehyde, 56 g that was employed directly in the next step without further purification.

d) 1-((1RS,4SR)-bicyclo[2.2.1]heptan-2-yl)hex-5-en-2-ol

Magnesium shavings (11 g, 0.458 mol) were magnetically stirred under anhydrous diethyl ether (20 ml), several drops of 4-bromo-1-butene were added to start the Grignard reaction, once initiated anhydrous diethyl ether (100 ml) was added followed by a solution of 4-bromo-1-butene 63.45 g, 0.47 mol) in anhydrous diethyl ether (200 ml). An exothermic reaction ensued and the rate of addition was such that a gentle reflux was maintained. Following the complete disappearance of the magnesium turnings, the suspension was allowed to cool to ambient temperature. Next, a solution of the aldehyde obtained under c) (54 g, 0.39 mol) in anhydrous diethyl ether (200 ml) was added slowly dropwise at such a rate to maintain a gentle reflux. The solution was stirred for a further 12 hours, then poured into a mixture of ice and saturated ammonium chloride. The mixture thus obtained was extracted with ether, washed with brine, dried over anhydrous sodium sulfate, filtered and the solvents removed in vacuo, to yield the alcohol with a yield of 91%.

$^1$H NMR: 5.90-5.79 (m, 1H), 5.08-4.95 (m, 2H), 3.69-3.57 (m, 1H), 2.28-2.06 (m, 4H), 2.00-1.89 (m, 1H), 1.82-1.73 (m, 1H), 1.64-1.00 (m, 12H), 0.67-0.57 (m, 0.7H).

$^{13}$C NMR: 138.7, 138.68 (d), 114.7, 114.72 (t), 71.0, 70.9, 70.3, 69.6 (d), 44.9, 44.7 (t), 41.9 (d), 40.9 (t), 40.7, 40.6 (d), 40.5 (t), 40.0 (t), 39.83, 39.82 (t), 38.7 (t), 38.4 (d), 37.9 (t), 37.3 (d), 37.14, 37.1 (t), 37.0, 36.9 (d), 36.8, 36.7, 36.6 (t), 36.5, 36.4, 36.3 (d), 35.4, 35.2 (t), 30.2 30.14, 30.12, 30.1 (t), 22.6, 22.5 (t).

e) 1-((1RS,4SR)-bicyclo[2.2.1]heptan-2-yl)hex-5-en-2-one

Pyridinium chlorochromate (60 g, 0.28 mol) was suspended in dichloromethane (500 ml) containing silica gel (200 g). After 15 minutes of mechanical stirring, a solution of the alcohol obtained under d) (35 g, 0.18 mol) in dichloromethane (200 ml) was added rapidly dropwise. After 60 minutes, a further portion of pyridinium chlorochromate (5.0 g) was added in one portion and the suspension stirred for a further 60 minutes, then diluted with ether (500 ml). Stirred for a further 15 minutes, then filtered through a plug of celite/silica. The filter cake was washed with ether and the combined filtrate was concentrated in vacuo to yield the crude ketone, 30.6 g as a green brown oil. Further purification by distillation using a Vigreux column 0.11 mbar 60-130° C. gave the desired ketone 21 g. Bulb to bulb distillation of the crude ketone at 130° C. at 0.11 mbar gave the pure ketone 15.5 g, 44.8%, as a mixture of endo:exo isomers (70:30).

$^1$H NMR: 5.86-5.75 (m, 1H), 5.05-4.99 (m, 1H), 4.97 (ddt, J=10.2, 1.7, 1.3, 1H), 2.52-2.36 (m, 3H), 2.35-2.11 (m, 4H), 1.94-1.88 (bm, 1H), 1.83 (dddd J=12.3, 11.9, 4.7, 3.0, 1H), 1.55-1.16 (m, 6H), 1.16-1.04 (m, 1H), 1.01-0.94 (m, 0.3H) and 0.58 (ddd, J=12.3, 5.3, 2.7, 0.7H) ppm.

$^{13}$C NMR: 210.4, 210.0 (s), 137.3 (d), 115.1 (t), 50.2, 46.3, 42.0 (t), 41.3, 40.2 (d), 39.8, 38.1 (t), 37.3, 37.1 (d), 36.9 (t), 36.8, 35.5 (d), 35.2, 30.0, 29.9, 28.5, 27.8, 22.8 (t).

Preparation of 1-((1RS,2SR,4SR)-bicyclo[2.2.1]heptan-2-yl)hex-5-en-2-one a) Methyl 4-((1RS,2SR,4SR)-bicyclo[2.2.1]heptan-2-yl)-3-oxobutanonate Under an atmosphere of nitrogen, sodium methoxide (15.61 g, 289 mmol) was suspended in dimethyl carbonate (120 mL). The mixture was heated under reflux and a solution of the 1-((1SRS,2R,4RS)-bicyclo[2.2.1]heptan-2-yl)propan-2-one (20 g, 131 mmol, see W. Reusch, J. Org. Chem., 1962, 27, 1882) in dimethyl carbonate (120 mL) was added slowly dropwise over 1 hour. The methanol formed was removed by azeotrope and the mixture heated under reflux for a further 3 hours, then cooled and concentrated to dryness in vacuo. The solid was partioned between saturated $NH_4Cl$ containing 10% HCl (5 mL) and ether. The aqueous phase was re-extracted with ether, and then the combined organic phase washed with saturated $NH_4Cl$, brine, dried over $Na_2SO_4$, filtered and concentrated in vacuo to give the crude ketoester. Further purification by distillation using a Vigreux column, 0.13 mbar b.p 70° C., gave the pure ketoester, 21 g.

$^{13}$C NMR: 202.4 (q), 167.7 (q), 52.3 ($CH_3$), 50.3 ($CH_2$), 49.2 ($CH_2$), 41.2 (CH), 38.0 ($CH_2$), 37.1 (CH), 36.7 (CH), 35.3 ($CH_2$), 29.8 ($CH_2$), 28.5 ($CH_2$).

b) Methyl 2-(2-(1RS,2SR,4SR)-bicyclo[2.2.1]heptan-2-yl)acetyl)pent-4-enonate

A mixture of potassium carbonate (6.85 g, 49.9 mmol) and sodium iodide (0.6 g, 4 mmol) were suspended in methanol (25 mL) and then heated to 50° C. to give a pale yellow solution. A solution of the ketoester obtained under a) (10.0 g, 47.6 mmol) in methanol (10 mL) was rapidly added, then stirred for a further 90 minutes at 50° C., then allyl chloride (4.65 mL, 57 mmol) was added over 5 minutes. The solution was heated at 50° C. for a further 15 hours. The suspension was cooled, then poured into $NH_4Cl$ and extracted twice with ether. The combined organic phase was washed with saturated $NH_4Cl$, brine, dried over $Na_2SO_4$, filtered and concentrated in vacuo to give the crude allyl ketoester. Further purification by bulb to bulb distillation 0.2 mbar 165° C. gave the desired allyl ketoester 8.65 g as a mixture of isomers (1:1).

$^{13}$C NMR: 204.2 (q), 169.7 (q), 134.3 (CH), 117.5 ($CH_2$), 58.5, 58.4 (CH), 52.4 ($CH_3$), 49.6, 49.5 ($CH_2$), 41.2, 41.0

(CH), 38.1, 38.0 (CH$_2$), 36.8, 36.7 (CH), 35.31, 35.29 (CH$_2$), 32.3, 32.2 (CH$_2$), 29.81, 29.78 (CH$_2$), 28.6, 28.5 (CH$_2$).

c) 1-((1RS,2SR,4SR)-bicyclo[2.2.1]heptan-2-yl)hex-5-en-one

The allyl ketoester (8.0 g, 32 mmol) was dissolved in ethanol (100 mL) containing potassium hydroxide (2.7 g, 47.9 mmol) and the solution heated under reflux for 2 hours to give a yellow solution. The solution was cooled, then concentrated to dryness. The residue was dissolved in water (50 mL) and conc HCl was added to give pH 2. This solution was heated at 60° C. for a further 45 minutes, then cooled. Extracted with ether (2×), the combined organic phase was washed with saturated NH$_4$Cl, brine, dried over Na$_2$SO$_4$, filtered and concentrated in vacuo to give the crude ketone 6.93 g as a pale yellow oil. Further purification by chromatography Puriflash cartridge (Si-HP 80G) with cyclohexane:ethyl acetate (99:1) as eluent in which only pure fractions were combined gave the pure ketone 0.7 g as a colorless oil.

$^{13}$C NMR: 210.0 (q), 137.2 (CH), 115.1 (CH$_2$), 50.2 (CH$_2$), 42.0 (CH$_2$), 41.3 (CH), 38.1 (CH$_2$), 37.4 (CH), 36.8 (CH), 35.3 (CH$_2$), 29.9 (CH$_2$), 28.6 (CH$_2$), 27.8 (CH$_2$).

Preparation of 2-(bicyclo[2.2.1]heptan-2-yl)hepta-1,6-dien-3-one a) 2-bicyclo[2.2.1]heptan-2-yl)acrylaldehyde The previously prepared aldehyde (5.5 g, 39.8 mmol) was suspended in formaldehyde solution (37% aqueous, methanol stabilized, 3.3 mL) and then heated rapidly to reflux. Dibutylamine (1.07 mL) was then added rapidly via syringe. The suspension was heated under reflux for a further 2 hours, then cooled. Extracted twice with ether, the combined organic phase was washed with water, then HCl (5%), then brine, dried over Na$_2$SO$_4$, filtered and concentrated in vacuo to give the crude enal, 4.5 g. (endo:exo, 2:1).

$^{13}$C NMR: 195.3, 195.2 (CH), 154.8, 151.4, (q), 133.5, 131.6 (CH$_2$), 40.6 (CH), 40.4 (CH$_2$), 39.7, 39.4, 39.0 (CH), 37.0 (CH), 36.7 (CH), 36.66 (CH$_2$), 35.7 (CH$_2$), 32.8, 30.0, 29.9, 28.8, 22.9 (CH$_2$).

b) 2-(bicyclo[2.2.1]heptan-2-yl)hepta-1,6-dien-3-ol

To magnesium pieces (1.08 g, 45 mmol) suspended and stirred in anhydrous ether (3 mL) was added 1,2 dibromoethane (several drops) followed by several drops of 4-bromo-1-butene. Once the Grignard formation was initiated, the remainder of the 4-bromo-1-butene (5.94 g, 44 mmol) in anhydrous ether (40 mL) was added slowly dropwise at a rate such that a gentle reflux was maintained. Following the consumption of the magnesium, the enal (4.4 g, 29.5 mmol) in anhydrous ether (40 mL) was added slowly dropwise. Allowed to attain reflux during the addition then stirred at ambient temperature for a further 2 hours. The solution was poured onto ice and saturated NH$_4$Cl. Extracted twice with ether, then the combined organic phase was washed with saturated NH$_4$Cl, brine, dried over Na$_2$SO$_4$, filtered and concentrated in vacuo to give the crude alcohol a mixture of isomers, 6.1 g. Further purification by bulb to bulb distillation 0.1 mbar 150° C. gave the pure alcohol as a mixture of endo:exo (2:1) isomers and 1:1 diastereoisomers, 5.05 g.

$^{13}$C NMR: 157.4, 153.3, 152.4, 138.6, 138.5, 138.4, 114.8, 114.78, 109.9, 108.6, 107.2, 106.5, 75.2, 75.1, 74.4, 74.3, 43.7, 43.5, 43.4, 43.1, 41.9, 40.9, 40.6, 40.5, 40.4, 40.0, 38.8, 37.7, 37.1, 36.6, 36.4, 36.2, 35.8, 35.3, 35.2, 35.2, 34.8, 33.8, 33.4, 30.5, 30.4, 30.2, 30.2, 30.1, 30.0, 28.7, 28.6, 22.9, 22.8.

c) 2-(bicyclo[2.2.1]heptan-2-yl)hepta-1,6-dien-3-one

The alcohol mixture (5.0 g, 24.3 mmol) in pentane (5 mL) was added in one portion to a stirred suspension of manganese dioxide (42 g, 485 mmol) in pentane (250 mL) and stirred for 2 hours at ambient temperature. A further portion of manganese dioxide (20 g) was added and the suspension stirred for a further 30 minutes at ambient temperature, then filtered through a pad of celite and rinsed with pentane. The solvents were removed in vacuo to yield the crude ketone, 4.11 g as a pale yellow oil. Bulb to bulb distillation at 140° C. at 0.1 mbar then gave the desired enone 3.53 g as a mixture of endo and exo isomers (7:3).

$^{13}$C NMR: 202.3, 201.8, 153.2, 150.2 (q), 137.5, 137.4 (CH), 121.9, 120.4, 115.1, 115.08 (CH$_2$), 41.4, 41.1, 40.7 (CH), 40.5 (CH$_2$), 40.0 (CH), 37.7, 37.5, 37.4 (CH$_2$), 37.2, 36.8 (CH), 35.7, 33.1, 30.0, 28.8, 28.5, 28.46, 22.9 (CH$_2$).

Preparation of 1-((1SR,2RS,4RS)-bicyclo[2.2.1]heptan-2-yl)hept-6-en-3-one a) Mixture of (E/Z)-1-((1RS,4SR)-bicyclo[2.2.1]heptan-2-yl)hepta-1/2,6-dien-3-one A three necked 100 ml flask was fitted with a Kutscher-Steudel apparatus filled with saturated NaCl solution and toluene (5 mL). Piperidine (1.21 g, 14.25 mmol)) was added to a solution of benzoic acid (1.74 g, 14.25 mmol) in allylacetone (9.33 g, 95 mmol) and toluene (45 ml). (1SR,4SR) bicyclo[2.2.1]heptanes-2-carbaldehyde (5.90 g, 47.5 mmol) was added in one portion and the solution was heated under reflux for 90 minutes. The mixture was cooled at 25°, hydrolyzed with an aqueous 5% HCl solution (250 ml) and extracted twice with ether. The organic extracts were washed (H$_2$O, NaOH 5%, H$_2$O and brine, then dried over Na$_2$SO$_4$, filtered and concentrated in vacuo to give a yellow oil, 8.27 g). Bulb to bulb distillation at 90-115°/0.05 mbar afforded the enones, 7.56 g as a mixture of E/Z and α,β and β,γ double bond isomers.

$^{13}$C NMR: 208.6, 199.7, 199.6, 152.4, 152.1, 146.1, 137.9, 137.6, 137.4, 137.3, 137.2, 137.1, 136.6, 136.0, 134.3, 133.2, 132.4, 129.4, 128.8, 115.1, 115.0, 110.4, 110.3, 50.7, 50.3, 49.7, 49.7, 48.0, 47.9, 45.6, 45.5, 44.4, 44.1, 42.9, 42.4, 42.2, 41.7, 41.4, 41.2, 41.0, 39.5, 39.1, 34.0, 32.7, 32.6, 31.7, 28.2, 28.1, 27.8, 27.7.

b) 1-((1RS,4SR)-bicyclo[2.2.1]heptan-2-yl)hept-6-en-3-one

Under an atmosphere of argon, 1,2 bis(diphenylphosphine) benzene (13.5 mg, 0.03 mmol, weighed in glove box) and Cu(OAc)—H$_2$O (60 mg, 0.3 mmol) were added to degassed and deoxygenated toluene (30 mL) to give a blue green solution that was rapidly stirred at ambient temperature for 10 minutes prior to the rapid introduction of PolyMethylHydroSilane (5.32 g, 89 mmol). The reaction mixture turned progressively from blue-green to yellow-green. After 20 minutes, the freshly distilled enone mixture obtained above (5.96 g, 29.5 mmol) was added via syringe. The reaction mixture became dark brown (after 5 minutes) and the temperature rose to ca. 35° C. After 15 hours at ambient temperature, the solvents were removed in vacuo, the residue was dissolved in THF (112 ml) and successively treated with HCl conc (0.446 ml) and H$_2$O (1.60 ml). The yellow solution was stirred at 50° for 2 hours. The solution was then cooled to ambient temperature, poured onto sat NaHCO$_3$ (150 ml), extracted twice with ether. The organic extracts were washed with brine, dried over Na$_2$SO$_4$, filtered and concentrated. Bulb to bulb distillation at 100-150°/0.05 mbar gave 7.47 g yellow liquid of mixture of desired ketone and unsaturated alcohols (fully saturated alcohol present <4%). Further purification by chromatography Puriflash cartridge (Si-HP 200G) with toluene:tetrahydrofuran (299:1 then 199:1 then 99:1, 49:1) as eluent gave the slightly impure desired ketone 1.65 g as a colorless oil followed by the alcohols resulting from 1,2 reduction various isomers. Further purification of the ketone by chromatography Puriflash cartridge (Si-HP 40G) with cyclohexane:ethyl acetate (98:2 then 99:1 then 97:3) as eluent gave the desired ketone (3:1, endo:exo) which was purified by bulb to bulb distillation at 100-105°/0.05 mbar 1.07 g.

$^{13}$C NMR: 210.7 (q), 137.2 (CH), 115.2 (CH$_2$), 41.9 (CH), 41.8 (CH$_2$), 41.4 (CH$_2$), 41.0 (CH), 38.0 (CH$_2$), 36.5 (CH), 35.2 (CH$_2$), 30.7 (CH$_2$), 30.0, 28.7, 27.8 (CH$_2$).

Preparation of 1-((1RS,4RS)-bicyclo[2.2.1]hept-5-en-2-yl)hex-5-en-2-one a)
(1RS,4RS)-5-(bromomethyl)bicyclo[2.2.1]hept-2-ene In a s/s autoclave, a mixture of cyclopentadiene dimer (71.7 g, 542 mmol) and allyl bromide (98 g, 813 mmol) was heated at 185° for 12 hours, then cooled. The mixture was concentrated in vacuo, then distilled 27-35° C. at 0.2 mbar to give the crude bromide 127 g. Fractional distillation 82-85° C. at 30 mbar gave the desired bromide 101.6 g as a mixture of endo:exo 85:15.

$^{13}$C NMR: 138.2, 131.6 (CH), 49.7 (CH$_2$), 45.5 (CH), 43.1 (CH), 42.1 (CH), 38.3, 32.8 (CH$_2$).

b) 1-((1RS,4RS)-bicyclo[2.2.1]hept-5-en-2-yl)hex-5-en-2-ol

To magnesium pieces (1.54 g, 63 mmol) suspended and stirred in anhydrous THF (3 mL) was added iodomethane (several drops) followed by several drops of the unsaturated bromide. The reaction was initiated by gentle heating to reflux, then a solution containing the remainder of the unsaturated bromide (10 g, 53.5 mmol) in anhydrous THF (40 mL) was added slowly dropwise at a rate such that a gentle reflux was maintained. Following the consumption of the magnesium, the solution was allowed to cool to ambient temperature, then the 4-pentenal (4.95 g, 58.8 mmol) in anhydrous THF (40 mL) was added slowly dropwise at such a rate as to maintain a gentle reflux. The mixture was stirred for a further 2 hours at ambient temperature, then the solution was poured onto ice and saturated NH$_4$Cl. Extracted twice with ether, then the combined organic phase was washed with saturated NH$_4$Cl, brine, dried over Na$_2$SO$_4$, filtered and concentrated in vacuo to give the crude alcohol as a mixture of isomers, 10.0 g as an orange oil. Further purification by chromatography PuriFlash SI-HP 80G with cyclohexane:ethyl acetate (99:1) as eluent gave the alcohol as a mixture of isomers (85:15 endo:exo and diastereoisomers), 1.5 g.

$^{13}$C NMR: 138.6, 137.3, 137.1, 132.5, 132.2 (CH), 114.7 (CH$_2$), 70.85, 70.8 (CH), 49.7, 49.5 (CH$_2$), 46.2, 45.3 (CH), 42.7 (2), 42.6 (CH), 42.5, 42.4 (CH$_2$), 37.0, 36.9 (CH$_2$), 35.2, 35.0 (CH), 32.7, 32.2 (CH$_2$), 30.1, 30.0 (CH$_2$), 26.9 (CH$_2$).

c) 1-((1RS,4RS)-bicyclo[2.2.1]hept-5-en-2-yl)hex-5-en-2-one

PCC (3.23 g, 15 mmol) was suspended in a vigorously stirred suspension of silica gel (4.0 g) in CH$_2$Cl$_2$ (50 mL). After 15 minutes, a solution of the alcohol obtained above (1.5 g, 7.8 mmol) in CH$_2$Cl$_2$ (10 mL) was added dropwise and the suspension was allowed to stir at ambient temperature for a further 3 hours. Then it was diluted with ether (30 mL) and was added celite (5 g) and then filtered through a pad of celite/silica. Washed with ether and the filtrate was concentrated in vacuo. Bulb to bulb distillation 160° c. at 0.4 mbar gave the desired ketone as a mixture of endo:exo isomers (85:15), 1.22 g.

$^{13}$C NMR: 210.4 (q), 137.8, 137.2 (CH), 132.2 (CH), 115.1 (CH$_2$), 49.7 (CH$_2$), 48.2 (CH$_2$), 45.7 (CH), 42.6 (CH), 42.0 (CH$_2$), 33.7 (CH), 32.4, 27.8 (CH$_2$).

Example 2

Preparation of a Perfuming Composition

A perfuming composition for liquid dish wash detergent was prepared by admixing the following ingredients:

| Ingredient | Parts by weight |
|---|---|
| Isobornyl acetate | 150 |
| Phenylethyl acetate | 20 |
| Styrallyl acetate | 20 |
| Aldehyde C 10 | 25 |
| Aldehyde C 8 | 10 |
| Hexylcinnamic aldehyde | 80 |
| Anethol | 10 |
| Ethyl 2-methyl-pentanoate [1] | 25 |
| Ethyl butyrate | 5 |
| Ethyl caproate | 10 |
| Lemon essential oil | 50 |
| Citronellyl nitrile | 25 |
| Verdyl acetate | 100 |
| Damascone Alpha | 10 |
| Dihydromyrcenol | 100 |
| Eucalyptus essential oil | 80 |
| 10% * Galbanum essential oil | 20 |
| Geraniol | 20 |
| Habanolide ® [2] | 100 |
| Hivernal ® [3] | 15 |
| Ocimene | 5 |
| Isoeugenol | 5 |
| Limette | 90 |
| Limonene | 350 |
| Linalool | 130 |
| Methyl methylanthranilate | 5 |
| Hedione ® [4] | 50 |
| Phenethylol | 60 |
| Alpha pinene | 50 |
| Rose oil | 30 |
| Amyle salicylate | 90 |
| Sclareolate ® [5] | 25 |
| Terpineol | 15 |
| 10% * Thymol | 10 |
| Verdox ® [6] | 200 |
| 2,4-Dimethyl-3-cyclohexene-1-carbaldehyde | 10 |
| | 2000 |

* in dipropyleneglycol
[1] origin: Firmenich SA, Geneva, Switzerland
[2] pentadecenolide; origin: Firmenich SA, Geneva, Switzerland
[3] 3-(3,3-dimethyl-5-indanyl)propanal mixture of 3-(1,1-dimethyl-5-indanyl)propanal; origin: Firmenich SA, Geneva, Switzerland
[4] methyl cis-dihydrojasmonate; origin: Firmenich SA, Geneva, Switzerland
[5] propyl (S)-2-(1,1-dimethylpropoxy)propanoate; origin: Firmenich SA, Geneva, Switzerland
[6] 2-tert-butyl-1-cyclohexyl acetate; origin: International Flavors & Fragrances, USA The addition of 100 parts by weight of 1-(bicyclo[2.2.1]heptan-2-yl)-hex-5-en-2-one (as a mixture endo/exo 70/30) to the above-described composition lifted the fragrance by boosting the fruity-pineapple/apple notes while imparting a freshness with its green note. When instead of the invention's compound it was used the same amount of 2-cyclohexyl-1,6-heptadien-3-one, then the effect was slightly metallic and much harder, aggressive and bitter as well as less natural, additionally the fruity note were only slightly modified. When instead of the invention's compound it was used the same amount of 2-cyclohexyl-1-cyclohexyl-5-hexen-2-one, the overall effect was just perceivable amongst the ananas notes of the original composition (e.g. allyl butyrate or caproate, ethyl 2-methyl-pentanoate, etc).

Example 3

Preparation of a Perfuming Composition

An eau de toilette for man was prepared by admixing the following ingredients:

| Ingredient | Parts by weight |
|---|---|
| Hexyl acetate | 10 |
| Citronellyl acetate | 10 |
| Geranyl acetate | 20 |
| 10% * Aldehyde C 10 | 20 |
| 10% * Ethyl 2-methyl-pentanoate [1] | 20 |
| 10% * Gamma undecalactone | 20 |
| Bergamote essential oil | 200 |
| Boisambrene Forte [2] | 15 |
| 10% * Calone ® [3] | 30 |
| Cashmeran ® [4] | 10 |
| Cedroxyde | 40 |
| 4-Cyclohexyl-2-methyl-2-butanol | 100 |
| Dimethyl benzyl carbinyl butyrate | 10 |
| Coumarine | 25 |
| 10% * Damascone alpha | 40 |
| Dihydromyrcenol | 570 |
| Ethylpraline | 10 |
| Ethylvanilline | 10 |
| Exaltolide ® [5] | 50 |
| Floralozone [6] | 10 |
| 3-(4-Methoxyphenyl)-2-methylpropanal | 25 |
| Gaiac | 10 |
| Geraniol | 20 |
| Habanolide ® [7] | 50 |
| Hivernal ® [8] | 100 |
| Iso E ® [9] Super | 800 |
| Isobutyrate de Cis-3-Hexenol | 5 |
| Lavander essential oil | 120 |
| Linalool | 200 |
| Mandarine essential oil | 40 |
| Muscenone Delta [10] | 40 |
| Hedione ® [11] | 100 |
| Nirvanol ® [12] | 10 |
| Patchouli oil | 50 |
| Orange essential oil | 100 |
| Romandolide ® [13] | 150 |
| Amyl salicylate | 50 |
| Cis-3-Hexenol salicylate | 10 |
| Sandela ® [14] | 30 |
| Sclareolate ® [15] | 60 |
| Terpineol Alpha | 30 |
| Trimofix ® [16] | 10 |
| 4-Methyl-3-decen-5-ol | 5 |
| Vanilline | 20 |
| 2-Tert-butyl-1-cyclohexyl acetate | 20 |
| 10% ** Violettyne [17] | 10 |
| 2,4-Dimethyl-3-cyclohexene-1-carbaldehyde | 5 |
| | 3200 |

* in dipropyleneglycol
** in isopropyl myristate
[1] origin: Firmenich SA, Geneva, Switzerland
[2] ethoxymethyl-cyclododecyl ether; origin: Kao Chemicals, Japan
[3] 7-methyl-2H,4H-1,5-benzodioxepin-3-one; origin: Firmenich SA, Geneva, Switzerland
[4] 1,2,3,5,6,7-hexahydro-1,1,2,3,3-pentamethyl-4-indenone; origin: Firmenich SA, Geneva, Switzerland

| Ingredient | Parts by weight |
|---|---|

[5] pentadecanolide; origin: Firmenich SA, Geneva, Switzerland
[6] 3-(4/2-ethylphenyl)-2,2-dimethylpropanal; origin: International Flavors & Fragrances, USA
[7] pentadecanolide; origin: Firmenich SA, Geneva, Switzerland
[8] 3-(3,3-dimethyl-5-indanyl)propanal mixture of 3-(1,1-dimethyl-5-indanyl)propanal; origin: Firmenich SA, Geneva, Switzerland
[9] 1-(octahydro-2,3,8,8-tetramethyl-2-naphtalenyl)-1-ethanone; origin: International Flavors & Fragrances, USA
[10] 3-methyl-5-cyclopentadecen-1-one; origin: Firmenich SA, Geneva, Switzerland
[11] methyl cis-dihydrojasmonate; origin: Firmenich SA, Geneva, Switzerland
[12] 3,3-dimethyl-5-(2,2,3-trimethyl-3-cyclopenten-1-yl)-4-penten-2-ol; origin: Firmenich SA, Geneva, Switzerland
[13] (1S,1'R)-[1-(3',3'-dimethyl-1'-cyclohexyl)ethoxycarbonyl]methyl propanoate; origin: Firmenich SA, Geneva, Switzerland
[14] 5-(2,2,3-trimethyl-3-cyclopentenyl)-3-methylpentan-2-ol; origin: Givaudan SA, Vernier, Switzerland
[15] propyl (S)-2-(1,1-dimethylpropoxy)propanoate; origin: Firmenich SA, Geneva, Switzerland
[16] mixture of 1-(2,6,10-trimethyl-1(2),5,9-cyclododecatrien-1-yl)-1-ethanone isomers; origin: International Flavors & Fragrances, USA
[17] 1,3-undecadien-5-yne;; origin: Firmenich SA, Geneva, Switzerland The addition of 100 parts by weight of 1-(bicyclo[2.2.1]heptan-2-yl)-hex-5-en-2-one (as a mixture endo/exo 70/30) to the above-described eau de toilette imparted to the latter a clear green-fruity twist reinforcing the lavender notes. The new fragrance acquired also a pleasant marine aspect.

When instead of the invention's compound it was used the same amount of 2-cyclohexyl-1,6-heptadien-3-one, then the effect was slightly metallic and was much harder, green/pyrazinic-galbanum, dry, aggressive and bitter as well as less natural and fruity, than the fragrance obtained with the invention's compound. No marine aspects were noted in such a case.

When instead of the invention's compound it was used the same amount of 2-cyclohexyl-1-cyclohexyl-5-hexen-2-one, the overall effect was fruitier, woman-like and without the green twist provided by the invention's compound. Furthermore, this fragrance had an impact much lower than the one with the invention's compound.

What is claimed is:
1. A compound of formula (I):

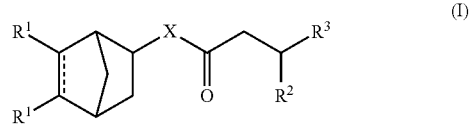

(I)

wherein the dotted line represents a carbon-carbon single bond or a carbon-carbon double bond;
one $R^1$ is a hydrogen atom and the other $R^1$ represents a hydrogen atom or a methyl or ethyl group;
X represents a C=$CH_2$ or C=$CHCH_3$ group or a $CHR^2$ or $CHR^2CHR^2$ group;
each $R^2$, independently from each other, represents a hydrogen atom or a methyl or ethyl group; and
$R^3$ represents a
a group of formula $CR^4$=$C(R^4)_2$, or
a group of formula (II)

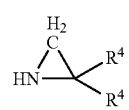

(II)

wherein $R^4$ represents, independently from each other, a hydrogen atom or a methyl or ethyl group; and wherein the compound is in the form of a pure enantiomer or a mixture thereof.

2. The compound according to claim 1, which is 1-(bicyclo[2.2.1]heptan-2-yl)-hex-5-en-2-one, 1-((1RS,4SR)-bicyclo[2.2.1]heptan-2-yl)hept-6-en-3-one or 1-((1RS,2SR,4SR)-bicyclo[2.2.1]heptan-2-yl)hex-5-en-2-one.

3. The compound of claim 1 which has 13 to 16 carbon atoms.

4. The compound according to claim 1, having formula (II):

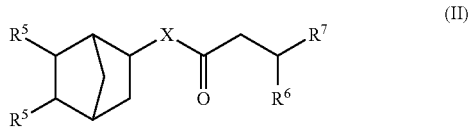

wherein one $R^5$ is a hydrogen atom and the other $R^5$ represents a hydrogen atom or a methyl group;
X represents a $C=CH_2$ or $C=CHCH_3$ group or a $CHR^2$ or $CHR^2CHR^2$ group;
each $R^6$, independently from each other, represents a hydrogen atom or a methyl group; and
$R^7$ represents a group of formula $CR^8=CHR^8$, each $R^8$, independently from each other, represents a hydrogen atom or a methyl group.

5. The compound according to claim 4, wherein compound (I) or (II) is in the form of a mixture of endo and exo diastereomers of the formulae

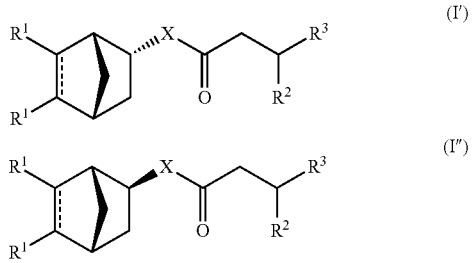

or respectively of the formulae

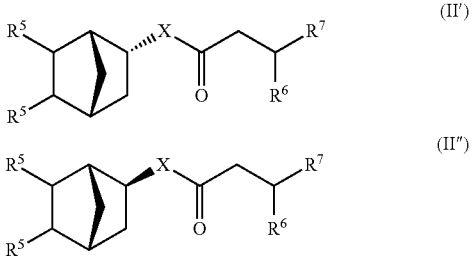

wherein $R^1$ to $R^7$, X and the dotted lines have the previously indicated meanings.

6. The compound according to claim 5, wherein the mixture of endo and exo diastereomers comprises at least 50% of diastereomer (I'), or (II'), the percentage being relative to the total weight of the mixture.

7. The compound according to claim 5, wherein X represents a $CHR^2$ or a $CHR^2CHR^2$ group, wherein each $R^2$ independently from each other, represents a hydrogen atom or a methyl group.

8. A perfuming composition comprising
i) at least one compound of formula (I), as defined in claim 1;
ii) at least one ingredient selected from the group consisting of a perfumery carrier and a perfumery base; and
iii) optionally at least one perfumery adjuvant.

9. The perfuming composition according to claim 8, wherein the compound has 13 to 16 carbon atoms and is added in an amount that imparts or confers a green allylic, glycolate and fruity-pineapple odor to the composition or article.

10. A perfuming consumer product comprising:
i) at least one compound of formula (I), as defined in claim 1; and
ii) a fine or functional perfumery base.

11. The perfuming consumer product according to claim 10, wherein the fine or functional perfumery base is a perfume, a fabric care product, a body-care product, an air care product or a home care product.

12. The perfuming consumer product according to claim 10, wherein the fine or functional perfumery base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oils or gel, a hygiene product, an air freshener, a "ready to use" powdered air freshener, a wipe, a dish detergent or hard-surface detergent.

13. The perfuming consumer product according to claim 10, wherein the compound has 13 to 16 carbon atoms and is added in an amount that imparts or confers a green allylic, glycolate and fruity-pineapple odor to the composition or article.

14. A method to confer, enhance, improve or modify the odor properties of a perfuming composition or of a perfumed article, which method comprises adding to said composition or article an effective amount of at least a compound of formula (I):

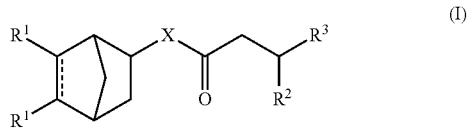

wherein the dotted line represents a carbon-carbon single bond or a carbon-carbon double bond;
one $R^1$ is a hydrogen atom and the other $R^1$ represents a hydrogen atom or a methyl or ethyl group;
X represents a $C=CH_2$ or $C=CHCH_3$ group or a $CHR^2$ or $CHR^2CHR^2$ group;
each $R^2$, independently from each other, represents a hydrogen atom or a methyl or ethyl group; and
$R^3$ represents a
a group of formula $CR^4=C(R^4)_2$, or
a group of formula (II)

wherein R⁴ represents, independently from each other, a hydrogen atom or a methyl or ethyl group; and wherein the compound is in the form of a pure enantiomer or a mixture thereof.

15. The method according to claim 14, wherein the compound (I) is of formula (II):

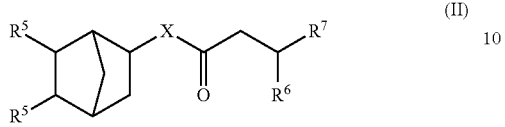

(II)

wherein one R⁵ is a hydrogen atom and the other R⁵ represents a hydrogen atom or a methyl group;

X represents a C=CH₂ or C=CHCH₃ group or a CHR² or CHR²CHR² group;

each R⁶, independently from each other, represents a hydrogen atom or a methyl group; and R⁷ represents a group of formula CR⁸=CHR⁸, each R⁸, independently from each other, represents a hydrogen atom or a methyl group.

16. The method according to claim 14, wherein compound (I) or (II) is in the form of a mixture of endo and exo diastereomers of the formulae

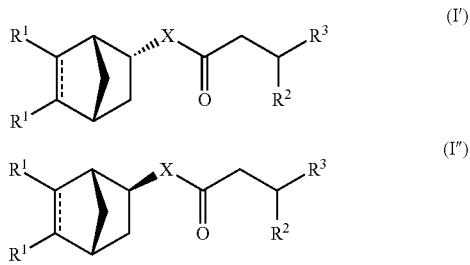

(I')

(I'')

or respectively of the formulae

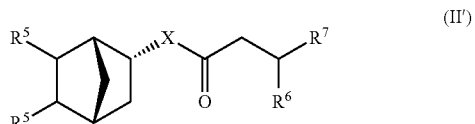

(II')

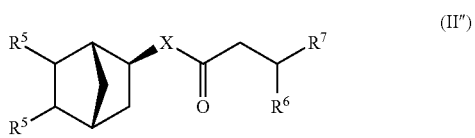

(II'')

wherein R¹ to R⁷, X and the dotted lines have the previously indicated meanings.

17. The method according to claim 16, wherein the mixture of endo and exo diastereomers comprises at least 50% of diastereomer (I'), or (II'), the percentage being relative to the total weight of the mixture.

18. The method according to claim 16, wherein X represents a CHR² or a CHR²CHR² group, wherein each R² independently from each other, represents a hydrogen atom or a methyl group.

19. The method according to claim 14, wherein the compound is 1-(bicyclo[2.2.1]heptan-2-yl)-hex-5-en-2-one, 1-((1RS,4SR)-bicyclo[2.2.1]heptan-2-yl)hept-6-en-3-one or 1-((1RS,2SR,4SR)-bicyclo[2.2.1]heptan-2-yl)hex-5-en-2-one.

20. The method according to claim 14, wherein the compound has 13 to 16 carbon atoms and is added in an amount that imparts or confers a green allylic, glycolate and fruity-pineapple odor to the composition or article.

* * * * *

UNITED STATES PATENT AND TRADEMARK OFFICE
CERTIFICATE OF CORRECTION

PATENT NO.         : 8,445,727 B2  
APPLICATION NO.    : 13/641931  
DATED              : May 21, 2013  
INVENTOR(S)        : Birkbeck It is certified that error appears in the above-identified patent and that said Letters Patent is hereby corrected as shown below:

In the Specifications:

Column 1:
Line 55, after "carbon-carbon" delete "single or".

Signed and Sealed this  
Twenty-third Day of July, 2013

Teresa Stanek Rea  
*Acting Director of the United States Patent and Trademark Office*